United States Patent
Sezginer et al.

(10) Patent No.: US 7,230,704 B2
(45) Date of Patent: Jun. 12, 2007

(54) DIFFRACTING, APERIODIC TARGETS FOR OVERLAY METROLOGY AND METHOD TO DETECT GROSS OVERLAY

(75) Inventors: Abdurrahman Sezginer, Los Gatos, CA (US); Hsu-Ting Huang, San Jose, CA (US); Kenneth Johnson, Santa Clara, CA (US)

(73) Assignee: Tokyo Electron Limited, Tokyo (JP)

( * ) Notice: Subject to any disclaimer, the term of this patent is extended or adjusted under 35 U.S.C. 154(b) by 276 days.

(21) Appl. No.: 10/858,691

(22) Filed: Jun. 2, 2004

(65) Prior Publication Data

US 2004/0246482 A1    Dec. 9, 2004

Related U.S. Application Data

(60) Provisional application No. 60/467,567, filed on Jun. 6, 2003.

(51) Int. Cl.
    *G01B 11/00* (2006.01)
(52) U.S. Cl. ..................................... 356/401
(58) Field of Classification Search ........ 356/399–401, 356/601, 622
    See application file for complete search history.

(56) References Cited

U.S. PATENT DOCUMENTS

| | | | |
|---|---|---|---|
| 4,378,159 A | 3/1983 | Galbraith | 356/237 |
| 4,757,207 A | 7/1988 | Chappelow et al. | 250/491.1 |
| 5,867,276 A * | 2/1999 | McNeil et al. | 356/445 |
| 6,023,338 A * | 2/2000 | Bareket | 356/401 |
| 6,458,605 B1 * | 10/2002 | Stirton | 438/7 |
| 6,462,818 B1 | 10/2002 | Bareket | 356/401 |
| 6,667,805 B2 | 12/2003 | Norton et al. | 356/326 |
| 7,170,604 B2 * | 1/2007 | Sezginer et al. | 356/400 |
| 2001/0007498 A1 * | 7/2001 | Arai et al. | 356/401 |
| 2002/0080364 A1 * | 6/2002 | Monshouwer et al. | 356/508 |
| 2002/0158193 A1 | 10/2002 | Sezginer et al. | 250/237 |
| 2003/0002043 A1 * | 1/2003 | Abdulhalim et al. | 356/400 |
| 2003/0021465 A1 | 1/2003 | Adel et al. | 382/151 |
| 2003/0021467 A1 | 1/2003 | Adel et al. | 382/151 |
| 2003/0042579 A1 * | 3/2003 | Schulz | 257/629 |
| 2003/0043372 A1 | 3/2003 | Schulz | 356/327 |

(Continued)

FOREIGN PATENT DOCUMENTS

WO    WO 02/069390 A2    9/2002

OTHER PUBLICATIONS

In re U.S. Appl. No. 10/613,378, by Sezginer et al., entitled "Overlay Metrology Method and Apparatus Using More Than One Grating Per Measurement Direction," filed Jul. 3, 2003, 31 pages in length.

(Continued)

*Primary Examiner*—Gregory J. Toatley, Jr.
*Assistant Examiner*—Isiaka O. Akanbi
(74) *Attorney, Agent, or Firm*—Stallman & Pollock LLP

(57) ABSTRACT

A method for measuring overlay in semiconductor wafers includes a calibration phase in which a series of calibration samples are analyzed. Each calibration sample has an overlay that is known to be less than a predetermined limit. A difference spectrum for a pair of reflectively symmetric overlay targets is obtained for each calibration sample. The difference spectra are then combined to define a gross overlay indicator. In subsequent measurements of actual wafers, difference spectra are compared to the overlay indicator to detect cases of gross overlay.

23 Claims, 11 Drawing Sheets

U.S. PATENT DOCUMENTS

| | | | |
|---|---|---|---|
| 2003/0044702 A1 | 3/2003 | Schulz | 430/30 |
| 2003/0133102 A1* | 7/2003 | Opsal | 356/237.1 |
| 2003/0160960 A1* | 8/2003 | Noguchi et al. | 356/401 |
| 2003/0190793 A1 | 10/2003 | Brill et al. | 438/401 |
| 2003/0223630 A1 | 12/2003 | Adel et al. | 382/145 |
| 2003/0224261 A1* | 12/2003 | Schulz | 430/22 |
| 2004/0066517 A1 | 4/2004 | Huang et al. | 356/509 |
| 2004/0137651 A1 | 7/2004 | Smedt et al. | 438/16 |

OTHER PUBLICATIONS

M. Adel et al., "Characterization of Overlay Mark Fidelity," *SPIE*, vol. 5038 (paper 5038-43), 2003, 8 pages in length.

W. Yang et al., "A Novel Diffraction Based Spectroscopic Method for Overlay Metrology," *PAPER-SPIE ML-02-Feb 20030 [SPIE's 28th Annual International Symposium and Education Program on Microlithography, Feb. 2003]*, pp. 1-9.

J. Bischoff et al., "Light Diffraction Based Overlay Measurement," *Metrology, Inspection, and Process Control for Microlithography XV, Neal T. Sullivan Editor [Proceedings of SPIE]*, vol. 4344 (2001), pp. 222-233.

P. Heimann, "The Color-Box alignment vernier: a sensitive lithographic alignment vernier read at low magnification," *Optical Engineering*, vol. 29, No. 7, Jul. 1990, pp. 828-836.

H-T Huang et al., "Scatterometry-Based Overlay Metrology," *Metrology, Inspection, and Process Control for Microlithography XVII, Proceedings of SPIE*, vol. 5038 (2003), pp. 126-137.

T.A. Germer, "Measurement of lithographic overlay by light scattering ellipsometry," *Surface Scattering and Diffraction for Advanced Metrology II, Proceeds of the SPIE*, vol. 4780 (2002) pp. 72-79.

SEMI P28-96, "Specification for Overlay-Metrology Test Patterns for Integrated-Circuit Manufacture," *specification SEMI P28-96, Semiconductor Equipment and Materials International*, San Jose, CA, 1996, 4 pages in length.

* cited by examiner

Fig. 5
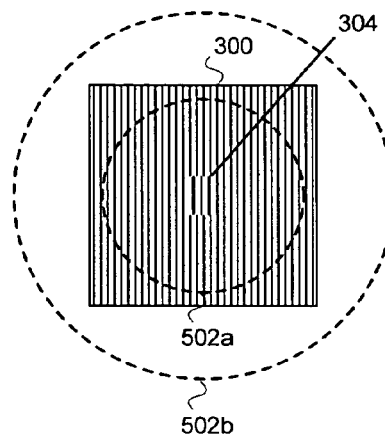
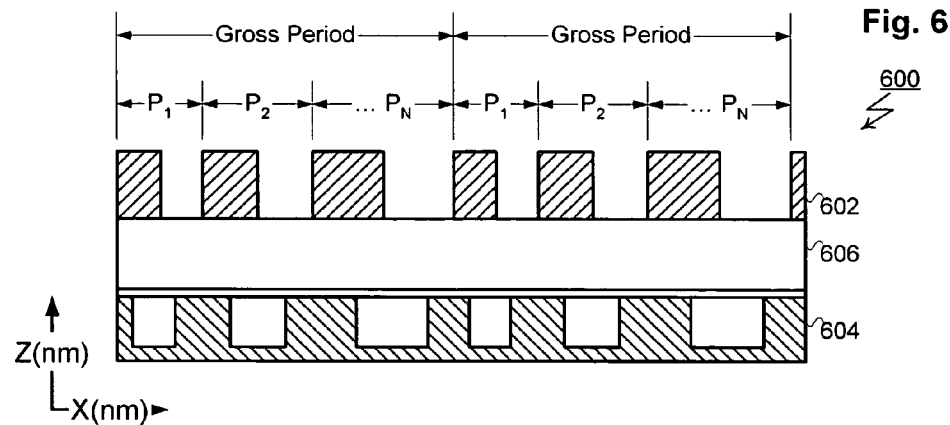
Fig. 6
Fig. 7
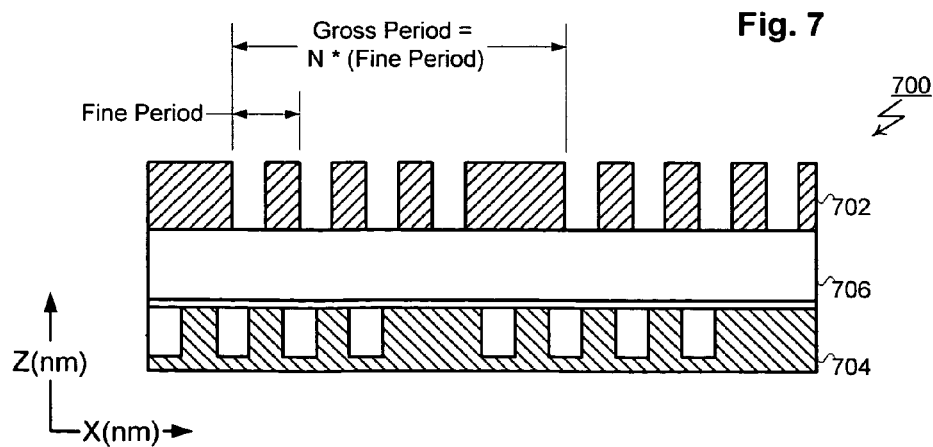

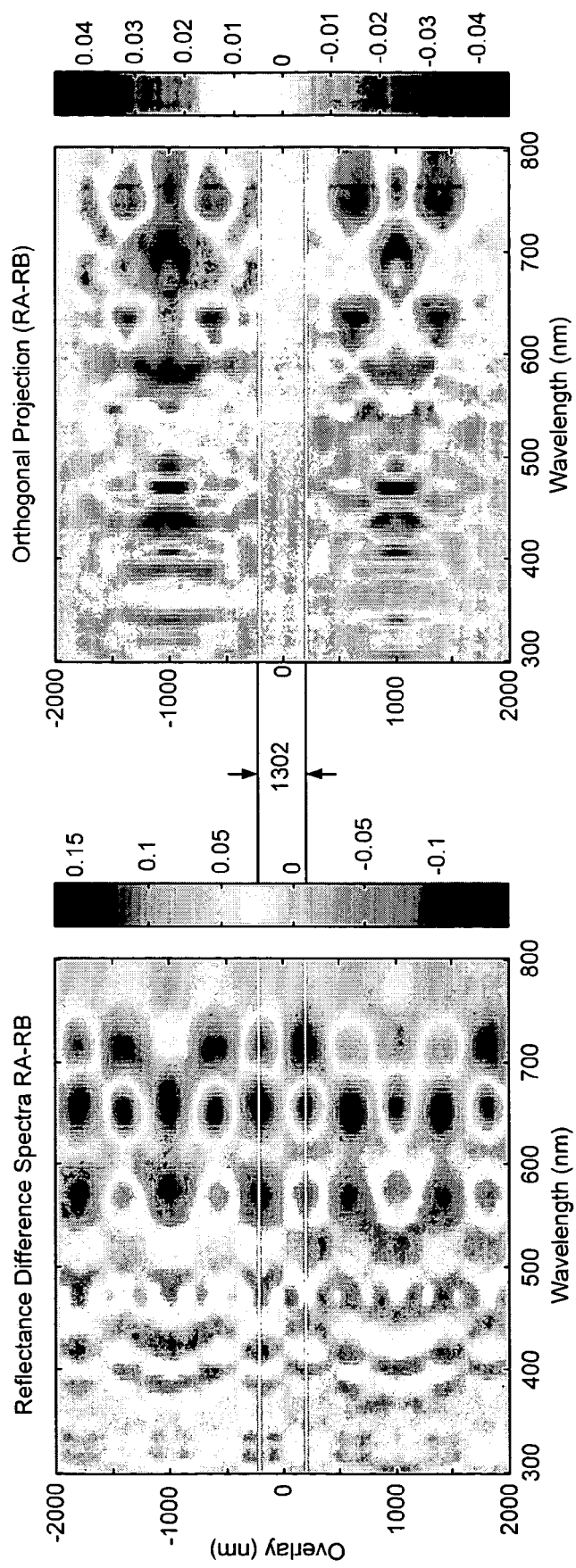

DIFFRACTING, APERIODIC TARGETS FOR OVERLAY METROLOGY AND METHOD TO DETECT GROSS OVERLAY

PRIORITY CLAIM

The present application claims priority to U.S. Provisional Patent Application Ser. No. 60/476,567, filed Jun. 6, 2003, which is incorporated in this document by reference.

RELATED APPLICATION

The subject matter of the present application is related to the disclosure included in a concurrently filed U.S. patent application Ser. No. 10/858,587 entitled: "APPARATUS AND METHOD FOR MEASURING OVERLAY BY DIFFRACTION GRATINGS". The disclosure of that related application is incorporated herein by reference.

TECHNICAL FIELD

This invention relates to measuring the pattern overlay alignment accuracy of a pair of patterned layers on a semiconductor wafer, possibly separated by one or more layers, made by two or more lithography steps during the manufacture of semiconductor devices.

BACKGROUND OF THE INVENTION

Manufacturing semiconductor devices involves depositing and patterning several overlaying layers. A typical semiconductor wafer might include, for example, a series of gates formed on a first layer and a series of interconnects formed on a second layer. The two layers (and their structures) are formed at different lithography steps in the manufacturing process. Alignment between the two layers is critical to ensure proper connection between the gates and their interconnects. Typically, this means that the tolerance of alignment must be less than the width of a single gate.

Overlay is defined as the displacement of a patterned layer from its ideal position aligned to a layer patterned earlier on the same wafer. Overlay is a two dimensional vector ($\Delta x$, $\Delta y$) in the plane of the wafer. Overlay is a vector field, i.e., the value of the vector depends on the position on the wafer. Perfect overlay and zero-overlay are used synonymously. Overlay and overlay error are used synonymously. Depending on the context, overlay may signify a vector or one of the components of the vector.

Overlay metrology provides the information that is necessary to correct the alignment of the stepper-scanner and thereby minimize overlay error with respect to previously patterned layers. Overlay errors, detected on a wafer after exposing and developing the photoresist, can be corrected by removing the photoresist, repeating exposure on a corrected stepper-scanner, and repeating the development of the photoresist. If the measured error is acceptable but measurable, parameters of the lithography process could be adjusted based on the overlay metrology to avoid excursions for subsequent wafers.

Most prior overlay metrology methods use built-in test patterns etched or otherwise formed into or on the various layers during the same plurality of lithography steps that form the patterns for circuit elements on the wafer. One typical pattern, called "box-in-box" consists of two concentric squares, formed on a lower and an upper layer, respectively. "Bar-in-bar" is a similar pattern with just the edges of the "boxes" demarcated, and broken into disjoint line segments. The outer bars are associated with one layer and the inner bars with another. Typically one is the upper pattern and the other is the lower pattern, e.g., outer bars on a lower layer, and inner bars on the top. However, with advanced processes the topographies are complex and not truly planar so the designations "upper" and "lower" are ambiguous. Typically they correspond to earlier and later in the process. The squares or bars are formed by lithographic and other processes used to make planar structures, e.g., chemical-mechanical planarization (CMP).

In one form of the prior art, a high performance microscope imaging system combined with image processing software estimates overlay error for the two layers. The image processing software uses the intensity of light at a multitude of pixels. Obtaining the overlay error accurately requires a high quality imaging system and means of focusing the system. One requirement for the optical system is very stable positioning of the optical system with respect to the sample. Relative vibrations blur the image and degrade the performance. Reducing vibration is a difficult requirement to meet for overlay metrology systems that are integrated into a process tool, like a lithography track.

As disclosed in U.S. patent application Ser. No. 2002/0158193; U.S. patent application 2003/0190793 A1; and as described in Proc. of *SPIE*, Vol. 5038, February 2003, "Scatterometry-Based Overlay Metrology" by Huang et al., p. 126–137, and "A novel diffraction based spectroscopic method for overlay metrology" by Yang et al. p. 200–207 (all four incorporated in this document by reference) one approach to overcome these difficulties is to use overlay metrology targets that are made of a stack of two diffraction gratings as shown in FIG. 1. The grating stack 10 has one grating 20 in a lower layer and another grating 30 in an upper layer as shown in FIG. 1. The layers of 20 and 30 are to be aligned. There are two instances of the grating stack 10, one for the x-component of overlay and one for the y-component. The measurement instrument is such that it does not resolve individual grating lines. It measures overall optical properties of the entire grating. Optical properties are measured as a function of wavelength, polar or azimuthal angle of incidence, polarization states of the illumination and the detected light, or any combination of these independent variables. An alternative embodiment uses two stacks of line gratings to measure x-overlay and two stacks of line gratings to measure y-overlay (four grating stacks total). Still another embodiment uses three line grating stacks in combination to simultaneously measure both x and y alignment. (See also PCT publication WO 02/25723A2, incorporated herein by reference). Scatterometry (diffraction) is proving to be an effective tool for measuring overlay.

A shortcoming of the prior scatterometry-based art is that, diffraction gratings cannot distinguish overlay values that differ by an integer number of periods. Let $R(\lambda,\theta,\xi)$ denote the specular (0-th order) reflection of the grating at wavelength $\lambda$, angle of incidence $\theta$, and offset $\xi$. The offset $\xi$ is the distance between centerlines of lower and upper grating lines as shown in FIG. 1. The function $R(\lambda,\theta,\xi)$ is periodic with respect to the offset $\xi$:

$$R(\lambda,\theta,\xi)=R(\lambda,\theta,\xi+P) \qquad (1)$$

where P is the period of the grating. The scatterometry-based overlay measurements are even more ambiguous when the profiles of the grating lines are symmetric. Then, a consequence of reciprocity is:

$$R(\lambda,\theta,\xi)=R(\lambda,\theta,-\xi) \qquad (2)$$

$$R(\lambda,\theta,(P/2)+\xi)=R(\lambda,\theta,(P/2)-\xi) \qquad (3)$$

There are two values of offset, separated by P/2, where the optical properties become ambiguous. Optical properties are insensitive to overlay at these points. Therefore, the largest measurement range is P/2 when the grating lines have symmetric cross-sections. When overlay exceeds this range, not only is the measurement wrong, there is no indication that the overlay is out of range. FIG. 2 demonstrates this ambiguity for calculated data corresponding to near-normal incidence, unpolarized reflectance of a grating stack as a function of offset $\xi$.

To overcome this limitation, Huang et al., cited above, describes a means of manufacturing a grating with an asymmetric unit cell. For gratings of that type (i.e., where there is substantial asymmetry) the measurement range becomes P, a whole period. The measurement range also becomes a whole period if two grating stacks are used, the offset of each stack is biased, and the two offset biases differ by P/4 (as described in U.S. application Ser. No. 10/613,378, filed Jul. 3, 2003, incorporated in this document by reference).

When the periodic nature of overlay is accounted for, the overlay measured by the grating, $\Delta x_{GRATING}$, is related to the actual overlay as follows:

$$N = \text{int}\left[\frac{\Delta x_{ACTUAL}}{P/2}\right] \Delta x_{GRATING} = (-1)^N [\Delta x_{ACTUAL} - NP/2] \quad (4)$$

In Equation (4), int[x] denotes the integer nearest to x. In prior art, the integer N is unknown. Therefore, $\Delta x_{GRATING}$ represents $\Delta x_{ACTUAL}$ only when N is zero, that is, when $|\Delta x_{ACTUAL}| < P/4$. $\Delta x_{GRATING}$, which is also called fine-overlay measurement, has high precision but it is only accurate when N=0. Gross overlay is defined as the condition $|\Delta x_{ACTUAL}| \geq P/4$ or $|\Delta y_{ACTUAL}| \geq P/4$, that is, any one component of overlay exceeding a quarter of the period. Gratings cannot detect gross overlay until overlay gets so large that the upper and lower gratings do not overlap in part of the measurement spot. Although gross overlay is rare in well-tuned lithography processes, alignment errors larger than 100 nm, even as large as several microns occur when a new process, a new reticle, or a new projector is introduced. In these instances, there is a need to not only detect but also to measure gross overlay.

Although increasing the period increases the measurement range, P/2, this approach is not preferred because it reduces the sensitivity of the optical response of grating stacks to overlay. As the period is increased, if the period becomes a significant fraction of the diameter of the measurement spot, the placement of the spot on the grating affects the overlay measurement and reduces its precision. For these two reasons, increasing the period to increase the measurement range is counter-productive. Using more than one grating stack, each with a different period, reduces but does not eliminate ambiguity.

SUMMARY OF THE INVENTION

The present invention provides a method and apparatus for analyzing overlay in semiconductor wafers. For a typical embodiment, a semiconductor wafer is patterned to include at least one pair of overlay targets for each direction for which overlay is to be measured. For the most common case, where overlay is measured in both X and Y directions, this means that a total of at least two pairs are used (one for X and one for Y directions). The overlay targets within a pair are configured to be reflectively symmetric when overlay is zero. This means that the overlay targets within a pair appear to be identical to an optical instrument (an instrument that measures the reflection of light as a function of wavelength, polar angle of incidence, azimuthal angle of incidence, polarization state, or any combination of these independent parameters) at zero overlay. When overlay is nonzero, the reflection symmetry within a pair is broken and the optical properties differ. For small values of overlay (typically up to 100 nm), the difference is directly proportional to overlay.

A calibration process is used to calculate a gross overlay indicator. For this process, a series of calibration samples are used. Each calibration sample includes the same overlay targets that are used for measuring overlay in actual wafers. Each calibration sample is also selected to have an overlay that is less than a predetermined limit. The calibration samples are inspected and a difference spectrum is constructed for each. Each difference spectrum represents the difference in reflectivity for the two halves of an overlay target pair. Typically, this is measured as a function of wavelength. So each difference spectrum will contain individual measurements obtained at a series of different wavelengths. The difference spectra of the calibration samples are combined to form a matrix S. The principal directions of S are obtained by finding the largest n nonzero eigen-values and the corresponding normalized eigen-vectors of matrix S. The principal directions are used to form a matrix Q. The gross overlay indicator is a function of Q.

During subsequent measurements on actual wafers, difference spectra are once again obtained by measuring pairs of overlay targets at multiple wavelengths. The difference spectra are then compared to the gross overlay indicator to determine if gross overlay is present. If not, then overlay may be computed as the difference spectra and a linear differential estimator.

A wide range of different instruments may be used to measure the reflectivity of the overlay targets used in the calibration samples and the wafers to be measured. One particularly suitable technique is to use an optical microscope in which the illumination and collection optics are configured so that the gratings of the overlay targets are resolved to have substantially uniform colors without resolving their unit cells.

BRIEF DESCRIPTION OF THE DRAWINGS

FIG. 5 shows alternate configurations for a measurement spot for the overlay target of FIG. 3A.

FIG. 6 shows a first embodiment of an overlay target that includes two pitches to support simultaneous measurement of gross and fine overlay.

FIG. 7 shows a second embodiment of an overlay target that includes two pitches to support simultaneous measurement of gross and fine overlay.

FIG. 13A is a map showing the difference spectrum $\Delta R$ as a function of wavelength and overlay for the overlay target of FIG. 7.

FIG. 13B is a map showing the orthogonal projection $(I-QQ^T)\Delta R$ as a function of wavelength and overlay for the overlay target of FIG. 7.

DETAILED DESCRIPTION OF THE PREFERRED EMBODIMENTS

The present invention provides one or more overlay targets along with a method for using the overlay targets to analyze overlay in semiconductor wafers. Together, the targets and analysis method increase the range of overlay that can be measured without sacrificing overlay measurement sensitivity. The following sections describe the targets first and then focus on the analysis method.

1. Description of the Overlay Target

Figure 1:
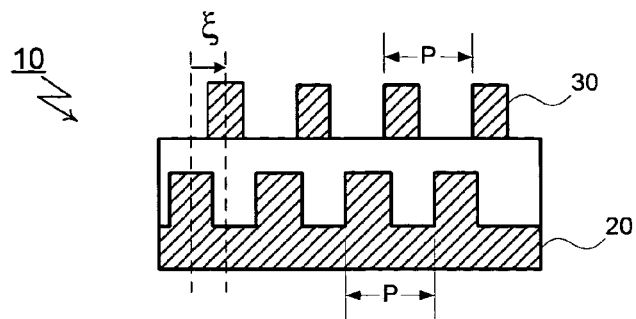
FIG. 1 shows in cross-section the stack of two gratings that are used in the diffraction-based overlay metrology in the prior art.
Figure 2:
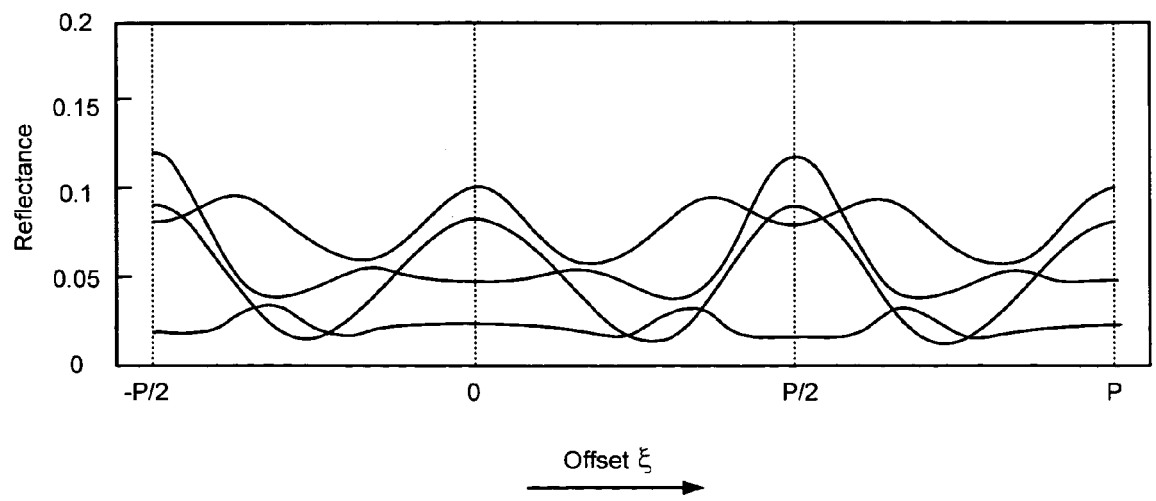
FIG. 2 shows calculated near-normal specular reflectance of the grating stack in FIG. 1 as a function of offset $\xi$ for four different wavelengths.
Figure 3A:
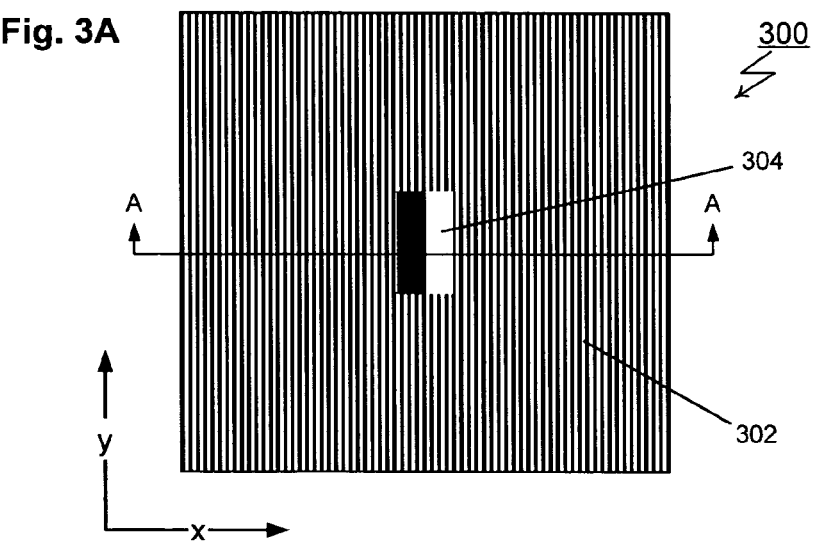
FIG. 3A shows an overlay target as provided by an embodiment of the present invention.

In FIG. 3A, a first embodiment of an overlay target as provided by the present invention is shown and generally designated 300. Target 300 is shown in the plan view (viewed in a direction that is perpendicular to the plane of the wafer) and includes a fine overlay pattern 302 and a gross overlay pattern 304. The gross overlay pattern 304 is used to measure or detect gross overlay and occupies a small fraction of the entire target 300.

Figure 3B:
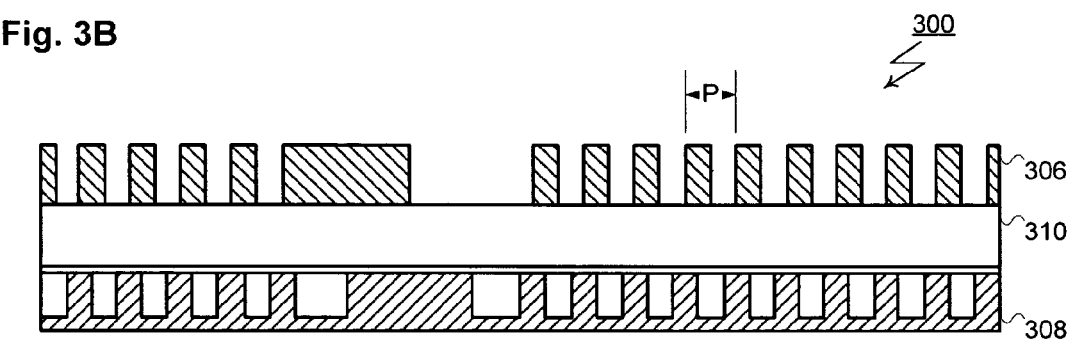
FIG. 3B shows a cross section of the overlay target of FIG. 3A.

FIG. 3B shows a cross section of target 300 taken along the line A—A in FIG. 3A. As shown by the cross-section, target 300 includes an upper grating 306 and a lower grating 308 that are formed in the two layers that are to be aligned. For lithography applications, upper grating 306 is typically part of the resist mask. Lower grating 308 is previously formed in a patterned layer, for example, in an isolation trench, gate, metal contact (via) or metal interconnection level. One or more intermediate layers 310 may be positioned between upper grating 306 and lower grating 308. The number of intermediate layers 310 and their compositions are application dependent.

Gross overlay pattern 304 can be implemented as a grating stack with a different pitch from the fine pitch P as shown in FIG. 3B. The line-to-space ratios in fine overlay pattern 302 and gross overlay pattern 304 may be different. The line-to-space ratios in upper grating 306 and lower grating 308 may also be different. Gross overlay pattern 304 can also be implemented as an aperiodic pattern without any periodicity in upper grating 306 or lower grating 308. By choosing a proper pitch and offset bias for gross overlay pattern 304, the higher pitch in gross overlay pattern 304 does not reduce the range in which a gross overlay is detected but improves the discrimination of both gross and fine overlay.

Figure 4:
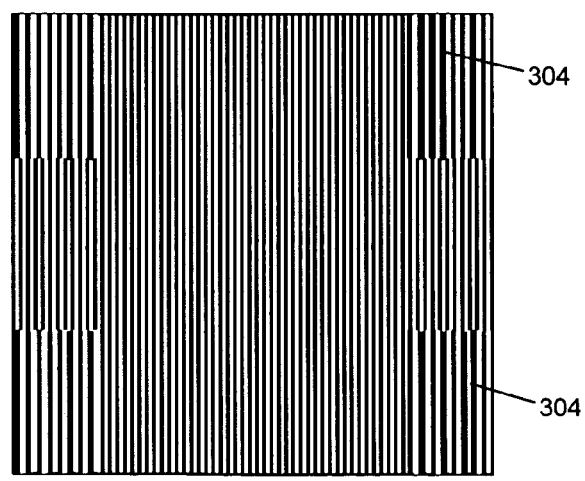
FIG. 4 shows alternate locations for a gross overlay feature within the overlay target of FIG. 3A.

For the implementation shown in FIGS. 3A and 3B, gross overlay pattern 304 breaks the periodicity of the fine grating pattern 302. FIG. 4 shows an alternate configuration where gross overlay pattern 304 is distributed at the corners of fine grating pattern 302.

Optical response of the overlay target is measured as a function of wavelength, polar angle of incidence, azimuthal angle of incidence, polarization state, or any combination of these independent variables. As shown in FIG. 5, the measurement spot can be smaller (502a) or larger (502b) than the overlay target 300. In either case, the gross overlay pattern 304 occupies a small fraction, such as 4%, of the area of the measurement spot. The more uniform the measurement spot, the higher is the tolerance to errors in positioning the spot. The overlay target in FIG. 4 has the gross overlay pattern 304 on the periphery of the target, and is not preferred for cases where the measurement spot is smaller than overlay target 300 (e.g., 502a).

In FIG. 6, a second embodiment of an overlay target as provided by the present invention is shown and generally designated 600. Target 600 includes an upper grating 602 and a lower grating 604 that are formed in the two patterned layers that are to be aligned. For lithography applications, upper grating 602 is typically part of the resist mask. Lower grating 604 is a previously formed patterned layer, for example, in an isolation trench, gate, metal contact (via) or metal interconnection level. One or more layers 606 may be positioned between gratings 602 and 604. The number of these intermediate layers 606 and their compositions are application dependent.

The lines in gratings 602 and 604 are configured to establish a repeating pattern. As shown in FIG. 6, the repeating pattern is composed of a series of gross periods. Each gross period is further composed of a series of fine periods (labeled $P_1$ through $P_N$ in FIG. 6). Each gross period is identical meaning that it includes the same series of fine periods. Gross periods are used to measure gross (micron-level) overlay while fine periods are used to measure fine overlay. For the particular example of FIG. 6, the gross period is 2455.38 nm. It is composed of a 615.38 nm fine period followed by an 800 nm period that is followed, in turn by a 1040 nm period. The fine periods are a geometric progression: the first is equal to $$\frac{800}{C}$$

nm, the second is 800 nm and the third is 800*C nm (where C is 1.3).

In general, it should be noted that the number of fine periods included in a gross period, as well as their sizes and line-to-space ratio is subject to endless variation. The important feature is that not all fine periods in one gross period are equal. For this particular example, each fine period has a line-to-space ratio of 1:1. For other implementations, different fine periods may be constructed to have different line-to-space ratios. Gratings 602 and 604 may also be constructed using different line-to-space ratios.

For the example of FIG. 6, the gross periods in gratings 602 and 604 are the same so that there are no Moire patterns across overlay target 600. Consequently, placement of the measurement spot on overlay target 600 is not critical for measurement spots smaller than the gross period. For scatterometry measurement, a typically measurement spot is on the order of 20 to 40 µm in diameter. The tolerance for positioning of the measurement spot within overlay target 600 is typically several micrometers.

In FIG. 7, a third embodiment of an overlay target as provided by the present invention is shown and generally designated 700. Target 700 includes an upper grating 702 and a lower grating 704 that are formed in the two patterned layers that are to be aligned. One or more intermediate layers 706 may be positioned between upper grating 702 and lower grating 704. Both upper grating 702 and lower grating 704 have a constant fine pitch. Depending on the implementation, the fine pitch may or may not be the same on both grating. Each gross period includes N fine periods. One of the N fine periods in every gross period has a line or space missing. In the example of FIG. 7, the fine period is 800 nm, the gross period is 4 µm and N=5.

Many other arrangements that are similar to those shown in FIGS. 6 and 7 are possible. The key feature of the targets is that there is a fine-scale structure to increase the sensitivity to overlay, and there is a gross-scale structure to measure or at least detect gross (on the order of a micrometer) overlay. The gross period is much smaller than the measurement spot of the optical instrument so that the target appears uniform (laterally homogeneous) to the optical instrument. This increases the tolerance to the position of the measurement spot relative to the target.

Figure 8:
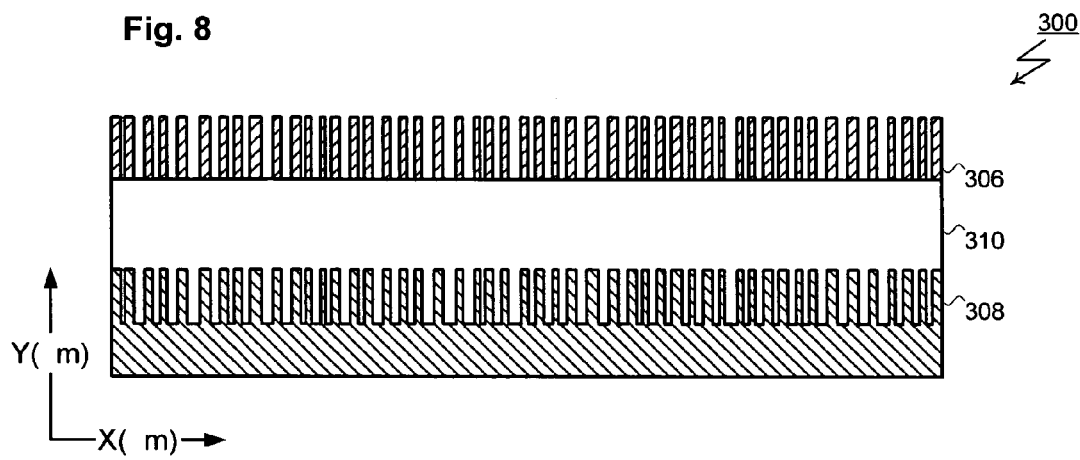
FIG. 8 shows an embodiment of an aperiodic overlay target.

FIG. 8 shows an overlay target 800 that has no gross-periodicity. In the pseudo-random implementation, the width of every line and space in layer 802 and 804 is randomly selected. In practice, the width of lines and spaces are randomly selected from a finite list since there is a minimum grid size for writing reticles.

2. Description of Overlay Measurement and Gross Overlay Detection

Figure 9:
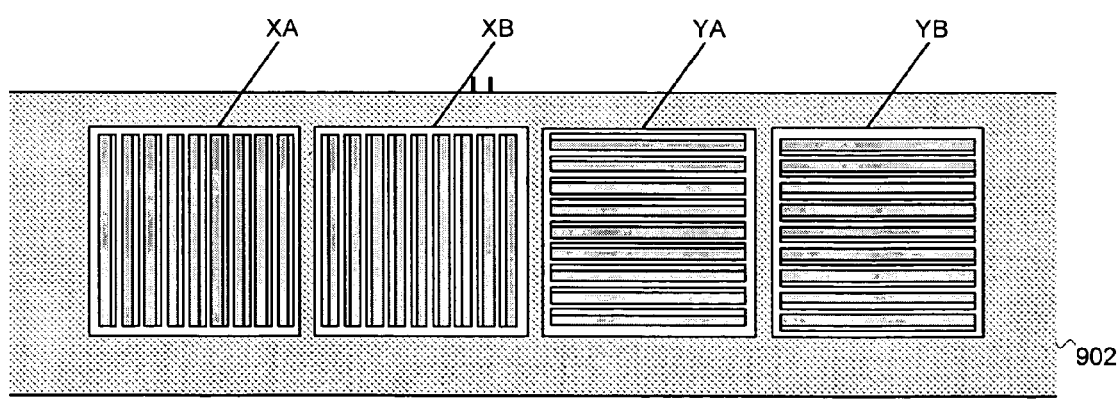
FIG. 9 shows two pairs of reflectively symmetric overlay targets enabling the simultaneous measurement of overlay in X and Y directions.

As shown in FIG. 9, four copies of an overlay target labeled XA, XB, YA, and YB are placed in close proximity of each other, preferably in a scribe line 902 between the dies on the wafer. Overlay targets XA, XB, YA, and YB may be selected from any of the types described above (i.e., overlay target 300, 600, 700 or 800). Overlay targets XA, XB, YA, and YB are measured with the optical instrument, one at a time or simultaneously. Targets XA and XB are used to obtain the overlay component Δx, and targets YA and YB are used to obtain another overlay component Δy.

The overlay targets XA and XB have reflective symmetry with respect to the x-axis when the x-component of overlay is zero. The lines of the fine gratings in XA and XB are parallel to the y-axis. Similarly, targets YA and YB have reflection symmetry with respect to the y-axis when the y-component of overlay is zero. The lines of the fine gratings in YA and YB are parallel to the x-axis.

For line gratings, reflection symmetry is equivalent to making a copy of a first target, rotating the copy by 180° in the plane of the wafer, and translating the copy in the plane of the wafer. The two overlay targets XA and XB look identical to an optical instrument (that measures the reflection of light as a function of wavelength, polar angle of incidence, azimuthal angle of incidence, polarization state, or any combination of these independent parameters) at zero overlay. When overlay is nonzero, the reflection symmetry is broken and the optical properties of target XA and XB differ. For small values of overlay (typically up to 100 nm), the difference is directly proportional to overlay.

Figure 10:
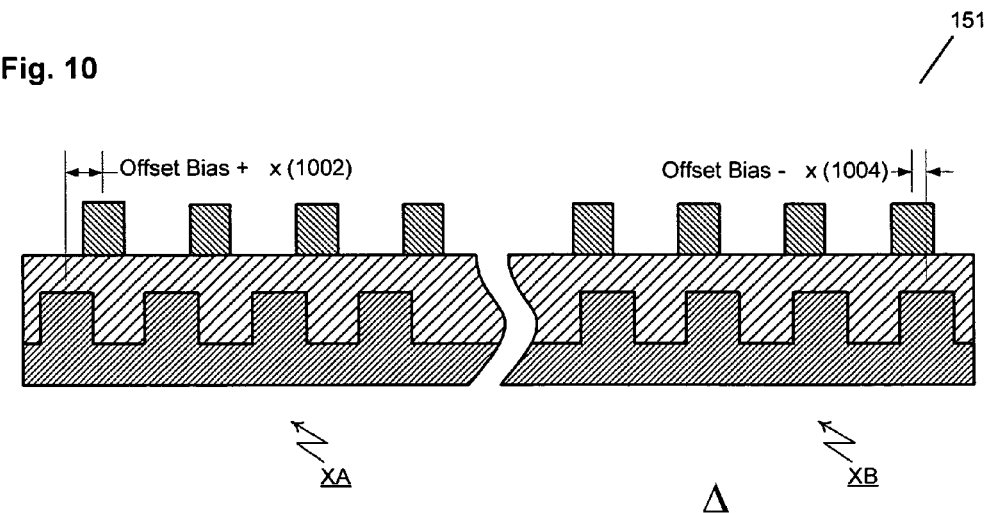
FIG. 10 is a cross-section of an embodiment of a reflectively symmetric overlay target.

Obtaining overlay from two targets (e.g., XA and XB) that only differ in the amount of offset between their upper and lower gratings increases the accuracy and precision of overlay that can be determined from optical response of the targets. FIG. 10 shows a cross section of two targets (XA and XB) configured in this fashion. The distance 1002 between the centerlines of the upper and lower grating lines in target XA is equal to the distance 1004 between the upper and lower grating lines in target XB at perfect alignment (zero overlay). When overlay Δx is nonzero, distance 1002 increases by Δx while distance 1004 decreases by Δx. Overlay targets XA and XB are identical in all respects other than the offset between their upper and lower gratings.

Reflection symmetry of target XA and XB leads to the property:

$$R_B(\lambda, \Delta x) = R_A(\lambda, -\Delta x) \quad (1)$$

$R_A(\lambda, \Delta x)$ and $R_B(\lambda, \Delta x)$ are optical responses of target XA and XB, respectively, for overlay Δx. Although we only explicitly show the dependence of $R_A$ and $R_B$ on wavelength λ, $R_A$ and $R_B$ can be a function of wavelength, polar angle of incidence, azimuthal angle of incidence, polarization state, or any combination of these independent parameters. The difference of the two spectra $R_A$ and $R_B$ is:

$$\Delta R(\lambda, \Delta x) = R_A(\lambda, \Delta x) - R_B(\lambda, \Delta x) \quad (2)$$
$$= 2\Delta x \frac{\partial R_A(\lambda, 0)}{\partial (\Delta x)} + \ldots$$

In the last equation, the first term in the Taylor series expansion with respect to a small overlay Δx is retained. Higher order terms are neglected. This approximation holds for |Δx|<100 nm for practical grating geometries. The left-hand side of Equation (2) is a measurable quantity that depends linearly on the parameter of interest, namely, the overlay Δx. Estimation of Δx from equation (2) takes the form of a linear operator on the difference spectrum:

$$\text{Estimate of } \Delta x = \Delta \hat{x} = \sum_\lambda LDE(\lambda) \Delta R_{MEAS}(\lambda) \quad (3)$$

Figure 11A:
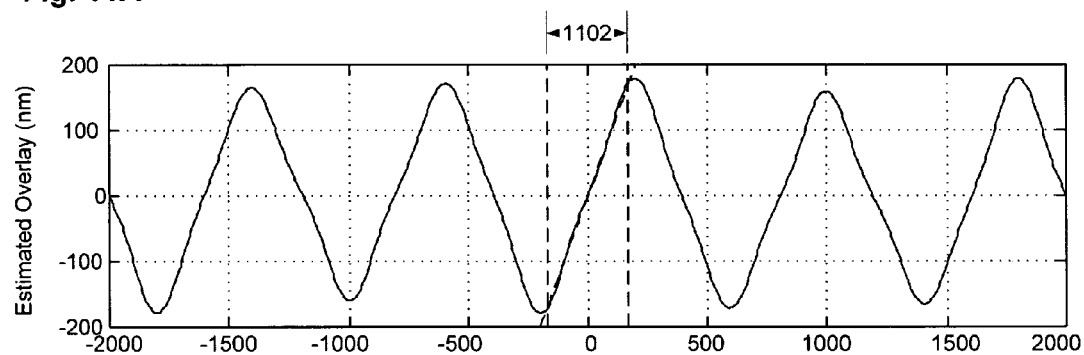
FIG. 11A is a plot showing estimated overlay as a function of actual overlay for the overlay target of FIG. 7.

The summation is over the discrete values of wavelength at which measurements are taken. $\Delta R_{MEAS}(\lambda)$ in Equation (3) is the difference of the reflection spectra measured for XA and XB. LDE(λ) is the so-called linear differential estimator. LDE(λ) is a spectrum that can be calculated by simulating diffraction of electromagnetic waves, or it can be obtained from measurements of targets with known overlay values. Equations (1) to (3) are prior art and they are repeated here for clarity. FIG. 11a shows the estimate Δx̂ of overlay obtained according to Equation (3) for the target described in FIG. 7. The estimate is valid in a linear range 1102 shown in FIG. 11*a*. Outside the linear range the estimate (3) is not valid. Modern lithography processes rarely make overlay excursions larger than 100 nm. In the event that overlay is outside the linear working range 1102, that condition must be flagged. The linear differential estimator (3) of the prior art provides no such warning.

The targets shown in FIGS. 3 though 8 have features that break the periodicity at the fine pitch. When the overlay is one or two times the fine period, the difference spectrum $\Delta R_{MEAS}(\lambda)$ is different than in Equation (2). This condition is detected by the following algorithm:

Step 1: Form the symmetric, positive semi-definite matrix S by adding rank-1 matrices $\Delta R(\Delta R)^T$.

$$S = \sum_{|\Delta x| < \delta} \Delta R (\Delta R)^T \quad (4)$$

The entries of the column vector $\Delta R$ are the measurements of the difference spectra at discreet wavelengths:

$$\Delta R = \begin{bmatrix} \Delta R_{MEAS}(\lambda_1) \\ \Delta R_{MEAS}(\lambda_2) \\ \vdots \\ \Delta R_{MEAS}(\lambda_M) \end{bmatrix} \quad (5)$$

$(\Delta R)^T$, which is a row vector, is the transpose of $\Delta R$. The summation in Equation (4) is over multiple training measurements where targets are known to have overlay values smaller than a predetermined threshold $\delta$ such as 100 nm. The training targets may have multiple values of offset smaller than $\delta$, and representative variations of other process parameters such as layer thicknesses and line widths.

Step 2: Find the largest n nonzero eigen-values and the corresponding normalized eigen-vectors $q_1, \ldots, q_n$ of matrix S. The eigen-vectors of S are called principle directions. The integer number n is a parameter of the algorithm. Its value is typically between 1 and 4. The matrix:

$$Q = [q_1 \ q_2 \ \ldots \ q_n] \quad (6)$$

has orthonormal columns. Store matrix Q for later use. This is the end of training.

Step 3: A gross overlay indicator (GOI) is obtained by the following operation during the measurement of overlay.

$$GOI = \|(I - QQ^T)\Delta R\| \quad (7)$$
$$= \left\| \Delta R - \sum_{j=1}^{n} q_j(q_j^T \Delta R) \right\|$$

GOI is a nonnegative scalar quantity. The double vertical bars in (7) indicate the Euclidian-norm of the vector. The vector $(I-QQ^T)\Delta R$ is the component of $\Delta R$ that is orthogonal to all principle directions $q_1, \ldots, q_n$. The projection matrix $P=(I-QQ^T)$ is the orthogonal projector of the linear space spanned by $q_1, \ldots, q_n$. Raise an alarm if GOI is larger than a previously determined threshold:

Gross overlay is detected if $GOI$>threshold $\quad (8)$

The value of the threshold is determined during training such that the alarm is not raised for any of the training cases.

Figure 11B:
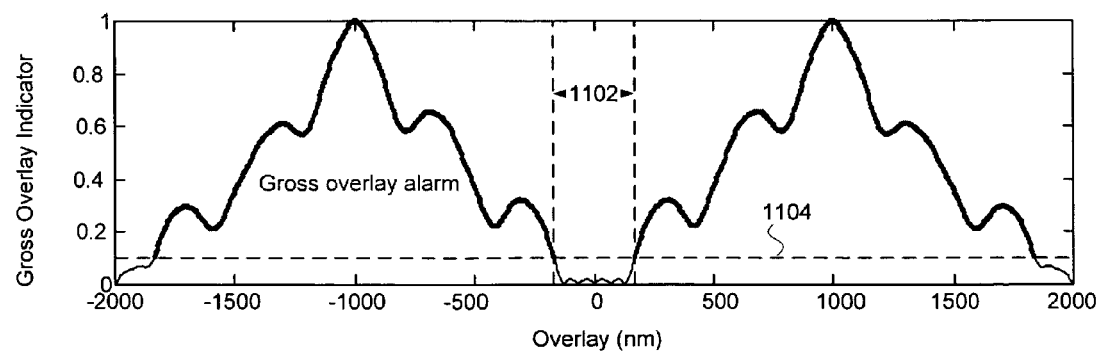
FIG. 11B is a plot showing a gross overlay indicator as a function of actual overlay for the overlay target of FIG. 7.

The gross overlay indicator GOI is shown as a function of overlay in FIG. 11*b* for the target described in FIG. 7. GOI is below a threshold 1104 in the linear working range 1102 where the linear differential estimation (3) is valid. For larger overlay values, GOI is above threshold 1104 indicating that estimation (3) should not be used. As overlay approaches (Gross Period)/2, GOI falls below threshold 1104 and no is longer an accurate indication of gross overlay. This happens for a 2 μm overlay for the target in FIG. 5. Such a large overlay can be detected by visual inspection using a visible light microscope.

Figure 12A:
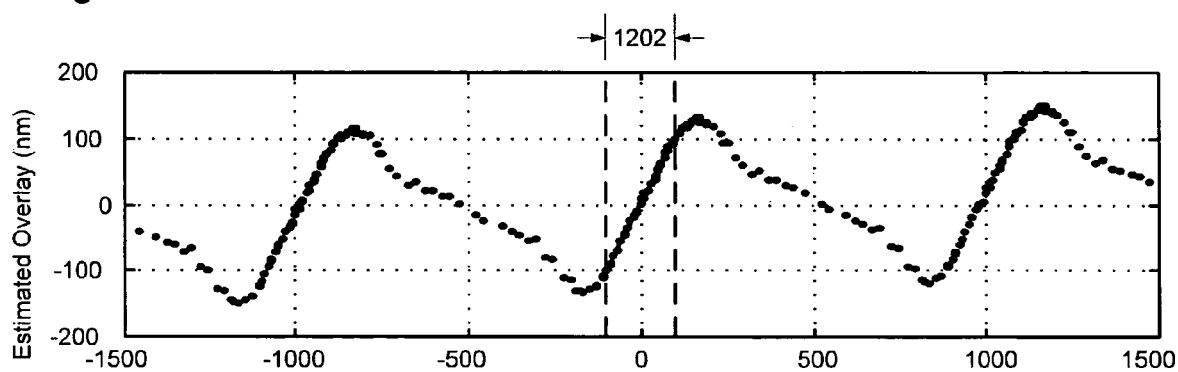
FIG. 12A is a plot showing estimated overlay as a function of actual overlay for the overlay target of FIG. 3A.
Figure 12B:
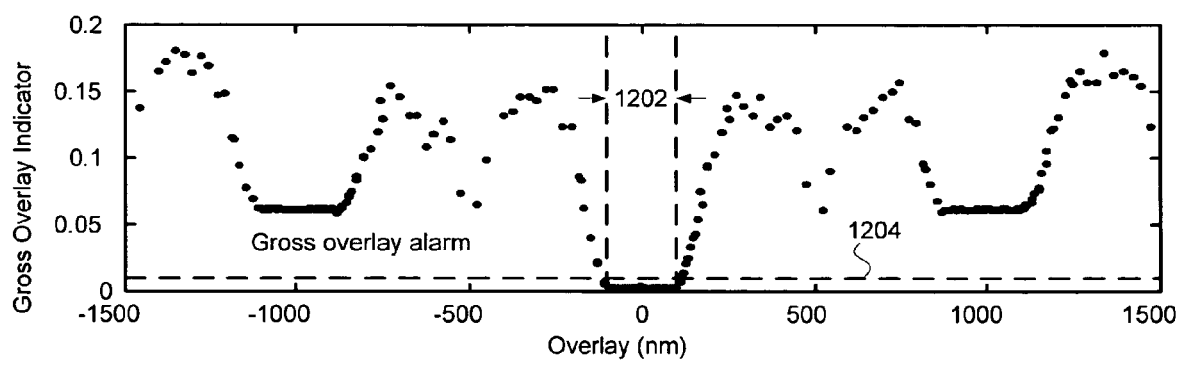
FIG. 12B is a plot showing a gross overlay indicator as a function of actual overlay for the overlay target of FIG. 3A.

The aperiodic target shown in FIGS. 3–5 has no periodicity. Therefore, the GOI will not return to zero for any large value of overlay. The GOI is shown as a function of overlay in FIG. 12*b* for the target described in FIG. 3*a*. The gross overlay pattern occupies 4% the area of the measurement spot. In this preferred overlay target, there is no fail of GOI (i.e., no false negative region) as that shown in FIG. 11*b*. For overlay values larger than the measurement range 1202, GOI is always above the threshold 1204. FIG. 12*a* shows the estimate $\Delta\hat{x}$ of overlay obtained according to Equation (3) for the target described in FIG. 3*a*.

This is why the gross overlay algorithm works: if the Taylor approximation in Equation (2) were exact, the matrix S would have only one nonzero eigen-value and all measured $\Delta R$ would be proportional to the corresponding principle direction, $q_1$. Then, $GOI = \|\Delta R - q_1(q_1^T \Delta R)\| = 0$ would be zero in the absence of noise. GOI would be zero in the linear regime where Equation (2) holds, and positive where $\Delta R$ is no longer linearly related to overlay. In reality, Equation (2) is not exact but GOI still discriminates between the linear regime where Equation (2) is a good approximation, especially if more than one principle direction is used (n>1).

Figure 14A:
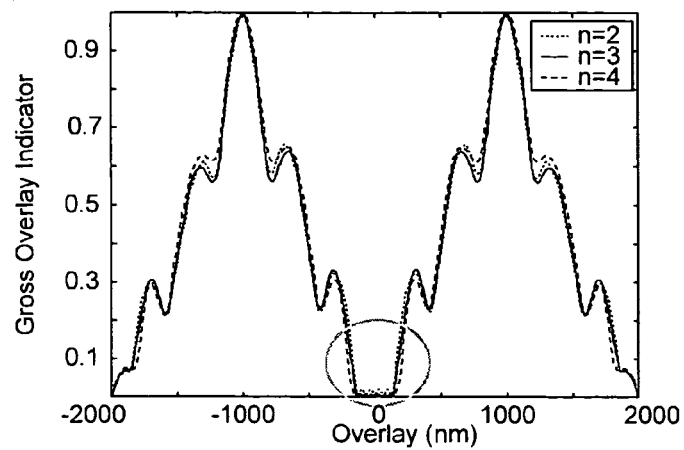
FIGS. 14A through 14C are plots showing gross overlay indicators as a function of actual overlay for n equal to 2, 3 and 4 where n is the number of principal directions used to compute the gross overlay indicator.
Figure 14B:
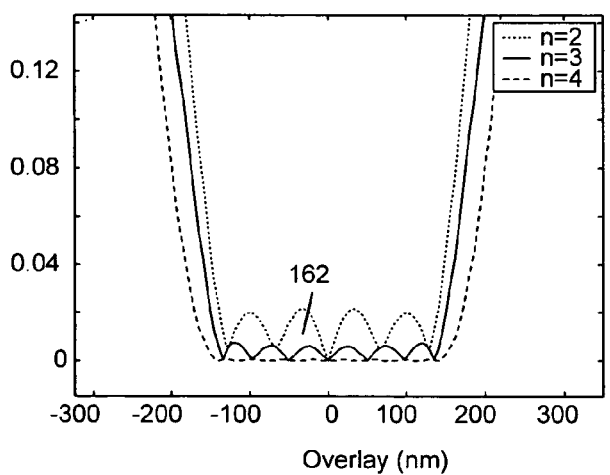

The map in FIG. 13*a* shows $\Delta R$ as a function of wavelength and overlay for the target in FIG. 7. The map appears almost periodic with respect to overlay with a period equal to the fine period (800 nm). $\Delta R$ deviates sufficiently from a periodic function. This is brought out in FIG. 13*b* where the orthogonal projection $(I-QQ^T) \Delta R$ is plotted as a color map as a function of wavelength and overlay. The resulting map is close to zero in the linear working range 1302. The gross overlay shown in FIG. 10*b* is obtained from the map in FIG. 13*b* by the operation $\|(I-QQ^T)\Delta R\|$. This amounts to squaring the map in FIG. 13*b*, summing the squares along the wavelength dimension, and taking the square root of the sum. The GOI in FIG. 11*b* is close to zero in the working linear range 1102 because the map of $(I-QQ^T)\Delta R$ is close to zero in the linear working range 1302 in FIG. 13*b*. FIGS. 14*a* and 14*b* show the effect of taking more principle directions. The GOI is closer to zero in the working linear range when more principle directions are taken. FIGS. 11*a* and 11*b* also show that very few principle directions are needed.

Figure 14C:
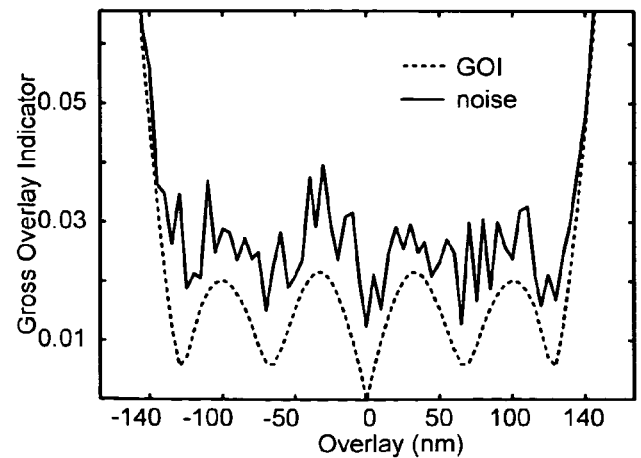

FIG. 14*c* shows two curves. The first is the gross overlay indicator GOI in the linear working range. No measurement noise was included in calculating GOI. The second curve shows GOI under typical noise of an actual near-normal spectroscopic reflectometer. As may be appreciated by inspection, discrimination of gross overlay from linear working range is robust under noise.

3. Description of Methods Using Multiple Targets for Overlay Metrology

The methods described in the previous section uses 4 overlay targets XA, XB, YA, and YB (as shown in FIG. 9)

to measure the X- and Y-components of overlay. The overlay can be obtained using Equation (3). The spectrum LDE($\lambda$) in Equation (3) can be calculated by simulating diffraction of electromagnetic waves, or it can be obtained from measurements of targets with known overlay values. The overlay targets XA and XB have reflection symmetry with respect to the x-axis when the x-component of overlay is zero. One way to implement XA and XB is to employ offset biases between the upper and lower gratings in overlay targets XA and XB. The offset biases in XA and XB have the same magnitude but opposite directions along the x-axis as shown in FIG. 10.

Figure 15:
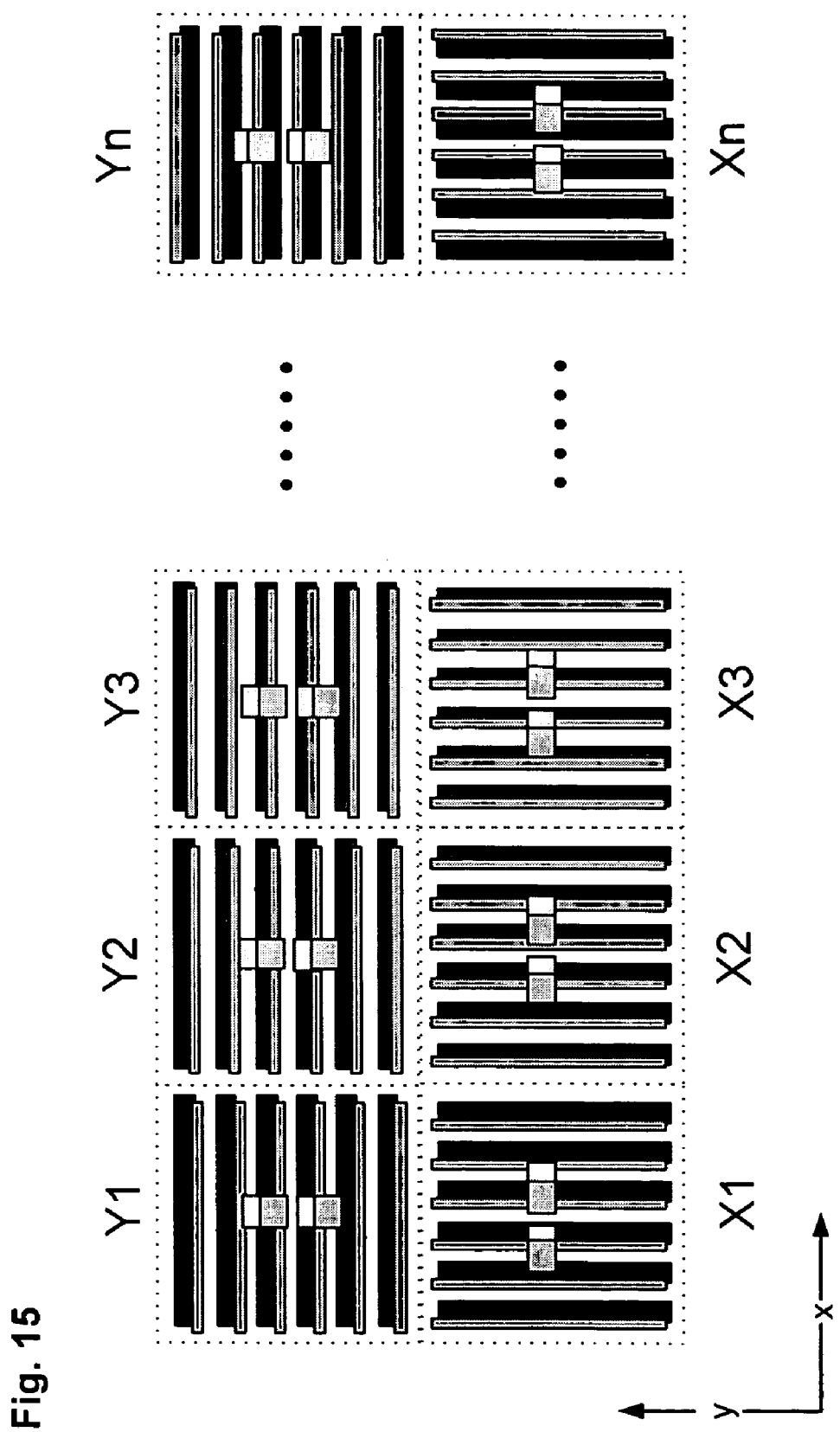
FIG. 15 shows an arrangement that includes multiple overlay targets as provided by an embodiment of the present invention.

Consider a set of overlay targets 302X1, 302X2, . . . , and 302Xn placed in close proximity as shown in FIG. 15. The overlay targets in 300 are lined up in FIG. 15, but they can actually be arranged in various ways. By choosing offset biases $\Delta X1, \Delta X2, \ldots,$ and $\Delta Xn$ for each target respectively, the total offsets in each target are $\Delta X1+\Delta x, \Delta X2+\Delta x, \ldots,$ and $\Delta Xn+\Delta x$ where $\Delta x$ is the overlay (alignment error). As long as these targets are close enough to one another (not necessarily adjacent to one another) on the wafer, the process conditions are the same for all targets. Therefore, the pattern profiles and layer thicknesses are essentially the same regardless of the different lateral offsets in each target. The optical response in each target $R_1, R_2, \ldots,$ and $R_n$ depends only on the total offset in each target and the optical instrument parameters:

$$R_i = R(\lambda, \Delta v) \qquad (4)$$

where $\lambda$ is the incident wavelength and $\Delta v = \Delta X_i + \Delta x$ is the total offset for the target Xi.

The optical instrument parameters can include wavelength, polar angle of incidence, azimuthal angle of incidence, polarization state, or any combination of these independent parameters. For targets with reflection symmetry to the lateral offset:

$$R(\lambda, \Delta v) = R(\lambda, -\Delta v) \qquad (5)$$

Figure 16A:
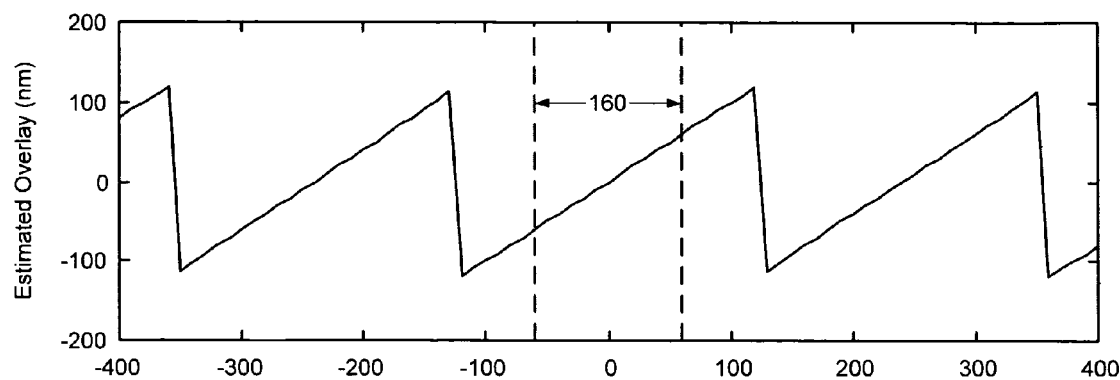
FIG. 16A is a plot showing estimated overlay as a function of actual overlay for the overlay target of FIG. 15.

With sufficient number of targets, the spectrum LDE($\lambda$) in Equation (3) can be obtained immediately from the measurements on these targets without any prior diffraction simulation or pre-measurements. Other interpolation methods can also be used to obtain overlay directly from measurements (e.g., see U.S. Provisional Application No. 60/519,345 and "The Color-Box Alignment Vernier: A Sensitive Lithographic Alignment Vernier Read At Low Magnification," Peter Heimann, *Optical Engineering*, July 1990, Vol. 29, No. 7, p. 828–836 (both incorporated in this document by reference). More terms in the Taylor expansion in Equation (2) can be included in the calculation if necessary as long as there are more measured targets than unknown quantities. FIG. 16a shows overlay estimation using 9 targets (as that shown in FIG. 5a or FIG. 5b) for each overlay component.

Figure 16B:
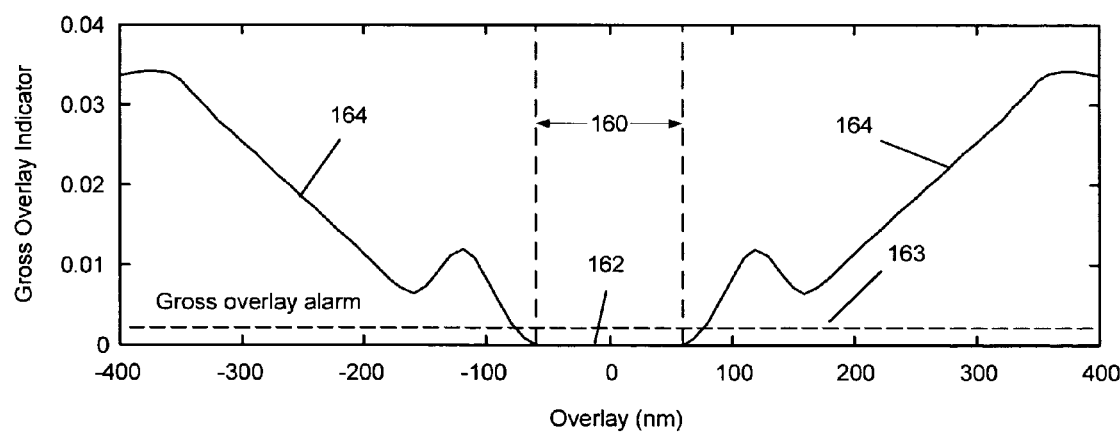
FIG. 16B is a plot showing a gross overlay indicator as a function of actual overlay for the overlay target of FIG. 15.

The gross overlay detect method described in the previous section can be directly applied to the case with multiple overlay targets. A simple way to implement it is to make two of the targets have the reflective symmetry described in Equation (1). The reflective difference of these two targets can be used to calculate the gross overlay indicator. FIG. 16b illustrates the GOI calculated from 2 of the 9 overlay targets using the Karhunen-Loeve expansion method described in the previous section. By proper choosing the offset biases $\Delta X_i$'s, more than one pair of reflection symmetry targets can be formed in a set of multiple overlay targets. A GOI with higher discrimination can be derived from these pairs of targets.

Figure 17:
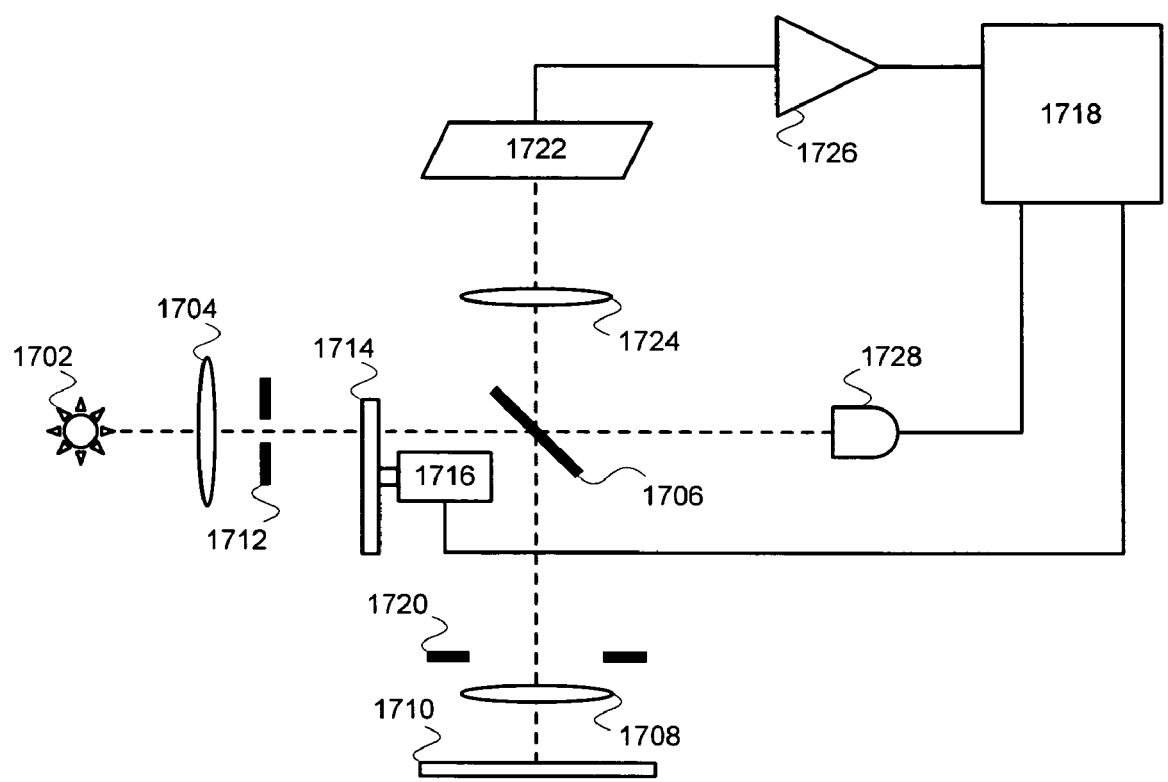
FIG. 17 is a block diagram of a metrology tool suitable for measuring overlay using the targets and methods provided by the present invention.

The multiple overlay targets 300 can be measured one-by-one in a series by any optical instrument suitable for scatterometry, such as an ellipsometer or reflectometer. The spectrum can be measured over different wavelengths, polar angles of incidence, azimuthal angles of incidence, or polarization states, et cetera. These multiple targets can also be measured simultaneously using an apparatus described in U.S. Provisional Application No. 60/519,345. For instance, imaging spectrometer 1700 in FIG. 17 can be used for the measurement purpose. It resolves the reflection from the wafer in the x-y plane of the wafer and in wavelength. In other words, the target is imaged at several wavelengths, either sequentially or simultaneously. The apparatus shown in FIG. 15 acquires images at different wavelengths sequentially.

Light from a broadband source 1702 is collected and collimated by optics 1704 before being directed by a beam splitter 1706 to an objective 1708. Objective 1708 then focuses the collimated illumination on a sample 1710. An aperture 1712 controls the numerical aperture of illumination ("illumination NA") and is preferably at a focal plane of objective 1708. A filter 1714 is positioned to select the wavelength at which the sample 1710 is illuminated. Preferably, filter 1714 is positioned in the collimated beam, downstream of optics 1704 and is preferably a band-pass interference filter with a bandwidth on the order of 10 nm. Other filters such as long-pass filters are also possible. Filter 1714 is mounted on a filter wheel that supports a multitude of filters with different pass bands. A motor 1716 rotates the filter wheel under the control of controller-processor 1718.

Sample 1710 includes an overlay target of the type described above. The overlay target is fully illuminated and the size of the illuminated spot on sample 1710 is controlled by a field stop 1720 in the illumination optics at a plane that is conjugate to the wafer. Aperture 1712 determines the collection NA for reflected light collected by objective 1708, and is preferably at a focal plane of objective 1708. Light collected by objective 1708 is imaged onto a detector array 1722 by an imager 1724. Optical elements 1704, 1708 and 1724 are schematically shown as single lenses in FIG. 17, but in practice they are compound reflective or refractive elements. The output of detector array 1722 representing the image of the sample 1710 is digitized by electronics 1726 and transmitted to controller-processor 1718. An algorithm that runs on 1718 processes images of the sample 1710 and returns overlay ($\Delta x, \Delta y$) and gross overlay indicator GOI for the x- and y-overlay. For cases with extremely large overlay error in one direction, the GOI for the other direction may also exceed threshold 162 shown in FIG. 14.

Apertures 1712 and 1720 control the imaging resolution of spectrometer 1700. The resolution is selected so that overlay targets 302X1, etc. (shown in FIG. 13) are resolved but their unit cells are not. The overlay targets are typically 10 $\mu$m×10 $\mu$m, and their units cells are typically sub-micron. Microscope objectives with NA larger than 0.5 can resolve 10 $\mu$m×10 $\mu$m features at visible wavelengths. It is preferable to limit the illumination NA with aperture 1720 to less than 0.1, for two reasons. The first reason is that the spectral (color) contrast between the overlay targets of different offsets is maximized by reducing the sum of the illumination and detection numerical apertures, because the diffracted colors of a grating depends on the angle of illumination and detection. The second benefit of a small illumination aperture is reduced cross talk between adjacent gratings stacks within the overlay target being imaged. The image of a grating stack has a diffraction tail in the image plane that extends beyond the bounds of the grating stack. The diffraction tails fall off faster when illumination NA is smaller than the collection NA.

Beam splitter 1706 splits the filtered illumination output of filter 1714 into a test beam and a monitor beam. A photodetector 1728 measures the intensity of the monitor beam, which is indicative of the intensity of the test beam that illuminates the targets. Detector array 1722 and photodetector 1728 preferably collect photons over the same time interval, where sequential collection is possible. Alternatively, detector 1728 could be an array into which the monitor beam is imaged (imaging optics not shown in FIG. 17). In yet another alternative, detector 1728 and array 1722 could be part of the same physical detector array, with mirrors and optics, not shown. The exposure (integration) time is preferably different for each setting of the filter. At the wavelengths where the light source is weaker or the detectors have smaller quantum efficiency, the integration time can be longer.

What is claimed is:

1. A method for optically inspecting and evaluating a test sample, said test sample having a plurality of layers formed by a lithography process, said test sample including a pair of reflectively symmetric overlay targets, the method comprising:
    obtaining individual difference spectrums for one or more calibration samples where each calibration sample includes a pair of reflectively symmetric overlay targets, where the difference spectrum is defined as the difference in reflectivity for the two overlay targets included in the reflectively symmetric pair and where the overlay of each calibration sample is known;
    constructing a gross overlay indicator from the difference spectrums of the calibration samples;
    obtaining a difference spectrum for the test sample;
    determining if the overlay of the test sample exceeds the predetermined limit using a function of the difference spectrum of the test sample and the gross overlay indicator; and
    adjusting the lithography process in response to the results of the determination step.

2. A method as recited in claim 1, that further comprises:
    forming a positive semi-definite matrix S as a summation of the difference spectrums of the calibration samples multiplied by their respective matrix transposes; and
    forming a matrix Q by finding the n largest nonzero eigen-values of S and the corresponding normalized eigen-vectors.

3. A method as recited in claim 1, in which each difference spectrum includes a series of measurements obtained at different wavelengths.

4. A method as recited in claim 1, in which the difference spectrum for a calibration or test sample is obtained by focusing a probe beam on the reflectively symmetric overlay targets within the calibration or test sample and gathering the reflected probe beam to obtain images of the two overlay targets included in the reflectively symmetric pair.

5. A method as recited in claim 4, in which each overlay target includes at least one grating stack and each image is obtained without resolving the unit cells of the grating stacks with each grating stack having a substantially uniform color within its image.

6. A method as recited in claim 4, in which each grating stack includes at least one aperiodic structure.

7. A method as recited in claim 4, in which each grating stack includes a fine overlay pattern and a gross overlay pattern.

8. An apparatus for optically inspecting and evaluating a test sample, said test sample including a pair of reflectively symmetric overlay targets, the method comprising:
    an illumination source that generates an optical probe beam;
    illumination optics configured to direct the probe beam to be reflected by the test sample;
    collection optics configured to gather some portion of the reflected probe beam and to form a corresponding image;
    a detector configured to convert the image formed by the collection optics into corresponding output signals; and
    a processor configured to:
        convert the output signals of the detector into a difference spectrum corresponding to the difference in reflectivity for said pair of reflectively symmetric overlay targets; and
        determining the gross overlay within the sample by comparing the difference spectrum with a gross overlay indicator obtained by evaluating a series of calibration samples where the overlay of each calibration sample is known.

9. An apparatus as recited in claim 8, where the processor is configured to obtain individual difference spectrums for the series of calibration samples by measuring the difference in reflectivity for a pair of reflectively symmetric overlay targets included in each calibration sample.

10. An apparatus as recited in claim 9, in which the processor is configured to form the gross overlay indicator by:
    forming a positive semi-definite matrix S as a summation of the difference spectrums of the calibration samples multiplied by their respective matrix transposes; and
    forming a matrix Q by finding the n largest nonzero eigen-values of S and the corresponding normalized eigen-vectors.

11. An apparatus as recited in claim 8, that further comprises one or more optical components for controlling the spectral content of the probe beam and where each difference spectrum includes a series of measurements obtained at different wavelengths.

12. An apparatus as recited in claim 8, in which the numerical aperture of the optics used to focus the probe beam is smaller than the numerical aperture of the optics used to gather the probe beam.

13. An apparatus as recited in claim 8, in which each overlay target includes at least one grating stack and each image is obtained without resolving the unit cells of the grating stacks with each grating stack having a substantially uniform color within its image.

14. An apparatus as recited in claim 13, in which each grating stack includes at least one aperiodic structure.

15. An apparatus as recited in claim 13, in which each grating stack includes a fine overlay pattern and a gross overlay pattern.

16. A method for optically inspecting and evaluating a test sample, said sample having a plurality of layers formed by a lithography process, the method comprising:
    obtaining a difference spectrum for the test sample where the difference spectrum corresponds to the difference in reflectivity for a pair of reflectively symmetric overlay targets included in the test sample;
    determining if the overlay of the test sample exceeds the predetermined limit using a function of the difference spectrum of the test sample and a gross overlay indicator; and adjusting the lithography process in response to the results of the determination step.

17. A method as recited in claim 16, that further comprises:
obtaining individual difference spectrums for one or more calibration samples each having a known overlay; and
constructing the gross overlay indicator from the difference spectrums of the calibration samples.

18. A method as recited in claim 17, that further comprises:
forming a positive semi-definite matrix S as a summation of the difference spectrums of the calibration samples multiplied by their respective matrix transposes; and
forming a matrix Q by finding the n largest nonzero eigen-values of S and the corresponding normalized eigen-vectors.

19. A method as recited in claim 16, in which each difference spectrum includes a series of measurements obtained at different wavelengths.

20. A method as recited in claim 16, in which the difference spectrum for a calibration or test sample is obtained by focusing a probe beam on the reflectively symmetric overlay targets within the calibration or test sample and gathering the reflected probe beam to obtain images of the two overlay targets included in the reflectively symmetric pair.

21. A method as recited in claim 20, in which each overlay target includes at least one grating stack and each image is obtained without resolving the unit cells of the grating stacks with each grating stack having a substantially uniform color within its image.

22. A method as recited in claim 20, in which each grating stack includes at least one aperiodic structure.

23. A method as recited in claim 20, in which each grating stack includes a fine overlay pattern and a gross overlay pattern.

* * * * *